US012687481B2

(12) United States Patent
Sublemontier et al.

(10) Patent No.: US 12,687,481 B2
(45) Date of Patent: Jul. 21, 2026

(54) METHOD FOR CHARACTERISING BIOLOGICAL PARTICLES IN AEROSOL FORM USING LASER-INDUCED PLASMA SPECTROMETRY AND ASSOCIATED SYSTEM

(71) Applicants:Commissariat a l'Energie Atomique et aux Energies Alternatives, Paris (FR); Centre National de la Recherche Scientifique, Paris (FR)

(72) Inventors: Olivier Sublemontier, Gif-sur-Yvette (FR); Jean-Philippe Renault, Gif-sur-Yvette (FR)

(73) Assignees: Commissariat a l'Energie Atomique et aux Energies Alternatives, Paris (FR); Centre National de la Recherche Scientifique, Paris (FR)

( * ) Notice: Subject to any disclaimer, the term of this patent is extended or adjusted under 35 U.S.C. 154(b) by 748 days.

(21) Appl. No.: 18/014,522

(22) PCT Filed: Jul. 9, 2021

(86) PCT No.: PCT/EP2021/069233
§ 371 (c)(1),
(2) Date: Jan. 5, 2023

(87) PCT Pub. No.: WO2022/008749
PCT Pub. Date: Jan. 13, 2022

(65) Prior Publication Data
US 2024/0044772 A1 Feb. 8, 2024

(30) Foreign Application Priority Data
Jul. 10, 2020 (FR) ...................................... 2007327

(51) Int. Cl.
*G01N 15/1434* (2024.01)
*G01N 15/01* (2024.01)
*G01N 33/68* (2006.01)

(52) U.S. Cl.
CPC ..... *G01N 15/1434* (2013.01); *G01N 33/6851* (2013.01); *G01N 15/01* (2024.01)

(58) Field of Classification Search
CPC ........... G01N 15/1434; G01N 33/6851; G01N 15/01; G01N 15/1459; G01N 2015/0046; G01N 21/718
See application file for complete search history.

(56) References Cited

U.S. PATENT DOCUMENTS

| 4,844,612 | A | * | 7/1989 | Durr | ...................... | G01N 21/73 |
| | | | | | | 356/316 |
| 6,359,687 | B1 | * | 3/2002 | Cheng | .................. | G01N 21/718 |
| | | | | | | 356/318 |

(Continued)

FOREIGN PATENT DOCUMENTS

| CN | 111044420 A | 4/2020 |

OTHER PUBLICATIONS

International Search Report issued in corresponding International Patent Application No. PCT/EP2021/069233 dated Sep. 22, 2021.

(Continued)

*Primary Examiner* — Seung C Sohn

(74) *Attorney, Agent, or Firm* — Morgan, Lewis & Bockius LLP

(57) ABSTRACT

The disclosure relates to a method for characterizing biological particles in aerosol form, such as suspended in an ambient gas, by laser-induced breakdown spectrometry and an associated system.

15 Claims, 6 Drawing Sheets

(56)            References Cited

U.S. PATENT DOCUMENTS

| | | |
|---|---|---|
| 10,393,587 B1 | 8/2019 | Yoo et al. |
| 2009/0053725 A1 | 2/2009 | Holwitt et al. |

OTHER PUBLICATIONS

Tjarnhage et al., "Development of a laser-induced breakdown spectroscopy instrument for detection and classification of single-particle aerosols in real-time," Optics Communications, 296: 106-108 (2013).

Ijaz et al., "Development of methods to study the survival of airborne viruses," Journal of Virological Methods, 18: 87-106 (1987).

Van Doremalen et al., "Aerosol and Surface Stability of SARS-CoV-2 as Compared with SARS-CoV-1," The New England Journal of Medicine (2020).

Hybl et al., "Laser-induced fluorescence-cued, laser-induced breakdown spectroscopy biological-agent detection," Applied Optics, 45 (34): 8806-8814 (2006).

Matsuda et al., "Statistical analysis on the distribution of alumina inclusion particles in ferritic stainless steels in laser-induced breakdown spectrometry using 1-kHz Q-switched Nd: YAG laser," Microchemical Journal, 153: 104400 (2020).

* cited by examiner

Ea

Eb

Ec

Ed

Ee

METHOD FOR CHARACTERISING BIOLOGICAL PARTICLES IN AEROSOL FORM USING LASER-INDUCED PLASMA SPECTROMETRY AND ASSOCIATED SYSTEM

TECHNICAL FIELD OF THE INVENTION

The present invention relates to the field of the characterisation of biological particles in the form of aerosols in an ambient gas.

The ambient gas can be in particular the surrounding air, inside a building or outside.

Today, the detection of biological particles in the air is currently done by sucking in the ambient air and accumulating the particles in a (small) volume of liquid or on gelatine filters. The presence of the sought biological particles is then checked by the method referred to as strip method or titrated by microscopy.

Alternatively, it is also possible to obtain aerosol deposits contained in the air, deposits which may contain biological particles. The presence in the deposit of a biological particle that is being sought is then established, using various techniques. There are many techniques that can be used, including in particular X-ray fluorescence and microscopy.

Thus, in the known techniques, we operate in two steps that are quite distinct in time but also in space, because they are carried out on quite different equipment, namely a collection step and a detection step.

The existing techniques are therefore time-consuming and, moreover, are not usually performed in situ.

SUMMARY OF THE INVENTION

One objective of the invention is to propose a solution for characterising the biological particles present in the form of an aerosol in a surrounding gas that is more efficient than the existing solutions.

In particular, the invention proposes a solution capable of providing a real-time and in situ characterisation of biological particles.

To this end, the invention proposes a method for characterising biological particles in aerosol form, i.e. suspended in an ambient gas, by laser-induced breakdown spectrometry, said method comprising the following steps:
- a) sampling ambient gas, which comprises the biological particles sought to be characterised;
- b) generating a jet of said particles in a chamber under vacuum;
- c) emitting a laser beam in the form of pulses and focusing said laser beam in said vacuum chamber transversely to a direction of propagation of the particle jet to create, in a focal volume, a plasma by the interaction between the laser beam and at most one individual particle of the jet, said plasma emitting other particles, characteristics of the interaction between the laser beam and said individual particle of the jet;
- d) collecting said particles emitted from the plasma; and
- e) performing a spectrometric analysis of these particles to finally characterise said biological particles.

The method according to the invention may comprise at least one of the following characteristics, taken alone or in combination:
- between the step a) and the step b), the following sub-steps are implemented:
- aa) introducing the ambient gas into a chamber (CHM) referred to as mixing chamber,

- ab) introducing into the mixing chamber, in the form of an aerosol, at least one type of receptor for a specific molecule of the biological particles sought to be characterised, said at least one type of receptor being otherwise marked,
- ac) mixing, in the mixing chamber, the aerosol comprising said at least one type of receptor marked with a molecule specific to the biological particles sought to be characterised with the sampled ambient gas and comprising said biological particles to be characterised;
- the aerosol comprising said at least one type of receptor marked with a molecule specific to the biological particles sought to be characterised;
- after the sub-step ac), the mixture formed is dried before implementing the step b);
- the marker being a magnetic material, after the sub-step ac), the only particles comprising this magnetic material are selected by any suitable magnetic means, before implementing the step b);
- said at least one type of receptor marked with a molecule specific to the biological particles sought to be characterised is obtained from a sprayed solution of said marked receptors;
- the solution is based on alcohol, for example ethanol;
- the step ab) consists of introducing into the mixing chamber, in the form of an aerosol, several distinct types of receptor for a specific molecule of the biological particles sought to be characterised, each type of receptor being marked;
- each type of receptor is marked differently.

To this end also, the invention proposes a system for implementing a method according to the invention, said system comprising:
- means for generating the aerosol of said at least one type of receptor marked with a molecule specific to the biological particles sought to be characterised;
- a mixing chamber comprising:
- a first inlet for the gas to be sampled,
- a second inlet for the aerosol generated by said means for generating an aerosol of said at least one type of receptor marked with a molecule specific to the biological particles sought to be characterised, and
- an outlet for mixing said aerosol comprising said at least one type of receptor marked with a molecule specific to the biological particles sought to be characterised with the sampled ambient gas and comprising said biological particles to be characterised;
- a device for characterising said particles by laser-induced breakdown spectrometry comprising:
- a system for generating, from the gas coming from the mixing chamber, the jet of said particles in a chamber to which is associated a means for pumping the gas present in the chamber in order to create a vacuum in this chamber, a laser capable of emitting the laser beam in the form of pulses, with which is associated an optical device arranged to focus said laser beam in the chamber, transversely to the direction of propagation of the jet of particles, and to create, in the focal volume, said plasma by the interaction between the laser beam and the particles of the jet, said plasma emitting other particles, characteristics of the interaction between the laser beam and said particles of the jet,
- at least one detection device comprising a means for collecting the particles emitted by the plasma and a means for performing a spectrometric analysis of these particles.

The system according to the invention may comprise at least one of the following characteristics, taken alone or in combination:

the mixing chamber comprises at least one dryer, arranged either between the means for generating the aerosol of the at least one type of marked receptor and the second inlet of the mixing chamber, or at the level of the outlet of the mixing chamber;

the mixing chamber is a Goldberg rotary drum;

the means for collecting the particles emitted by the plasma comprises a plurality of N optical fibres, with N a natural number strictly greater than the unity, one end of each optical fibre being arranged around the focal volume and pointing towards this focal volume to ensure the collection of the particles emitted by the plasma;

said optical fibres are mounted on an external wall, of spherical shape, of the chamber;

the means for performing a spectrometric analysis of the particles emitted by the plasma comprises:

a plurality of notch filters, capable of ensuring a filtering in a band of wavelengths distinct from each other, and a photodetector, for example of the electron photomultiplier type, associated with each notch filter;

BRIEF DESCRIPTION OF THE FIGURES

Further characteristics and advantages of the invention will become apparent from the following detailed description, for the understanding of which reference is made to the attached drawings, for which.

DETAILED DESCRIPTION OF THE INVENTION

In the following description, (O, X, Y, Z) defines a direct orthogonal reference frame.

Figures 1, 2:
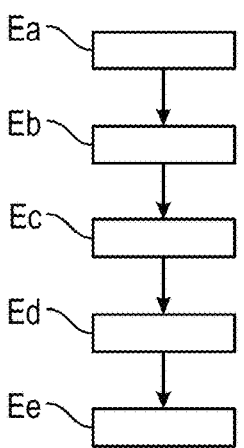
FIG. 1 is a schematic view of a method for characterising biological particles according to the invention.
FIG. 2 shows a cross-sectional view of a device for characterising biological particles in an aerosol operating by laser-induced breakdown spectrometry.

The invention relates in particular to a method, as illustrated schematically in FIG. 1, for characterising biological particles in aerosol form, i.e. suspended in an ambient gas, by laser-induced breakdown spectrometry. Biological particle means particles including cells, sub-cellular components, microbes such as bacteria, viruses, but also non-living macromolecules of biological origin, such as DNA, proteins, RNA. However, the method according to the invention is particularly well suited for biological particles with a small size, typically of the order of 100 nm. This is for example typically the size of the viruses.

The method comprises the following steps:

a) sampling ambient gas, which comprise the biological particles sought to be characterised (step Ea);

b) generating a jet of said particles JAB in a chamber CH under vacuum (step Eb);

c) emitting a laser beam FL in the form of pulses and focusing said laser beam in said vacuum chamber CH, transversely to a propagation direction of the particle jet JP, to create, in a focal volume VF, a plasma by the interaction between the laser beam FL and at most one individual particle $N_P$ of the jet, said plasma emitting other particles, characteristics of the interaction between the laser beam and said individual particle of the jet (step Ec);

d) collecting said particles emitted by the plasma (step Ed); and e) performing a spectrometric analysis of these particles to finally characterise said biological particles (step Ee).

In the step c), the laser beam FL may in particular be focused perpendicularly or substantially perpendicularly to the direction of propagation of the particle jet JP.

To implement the above method, a device D for characterising said particles by laser-induced breakdown spectrometry (LIBS), as shown in FIG. 2, may be employed.

The device D comprises a system SG for generating, from the gas coming from the sampler E, a jet of particles JP in a chamber CH with which is associated a means of pumping MP the gas present in the chamber in order to create a vacuum in this chamber. Typically, the pressure in the chamber CH can be in the order of 1 mbar or less for the characterisation of biological particles.

The system SG may for example comprise an aerodynamic lens LA, a chamber CH' vacuum by means of a pumping means MP' and advantageously a divertor ECO. The aerodynamic lens LA is fed, at the inlet ENT', with the gas sampled, and possibly diluted, from the sampler E, which may contain particles in aerosol form. At the outlet SORT' of the aerodynamic lens LA, a jet $J_G$ of particles in a carrier gas is then generated in the expansion chamber CH', in particular because it is under vacuum—typically the pressure may be of the order of 10 mbar or less for the characterisation of biological particles. The jet $J_{GP}$ of particles in a carrier gas is then passed through a divertor ECO which removes most of the carrier gas so that after the divertor, i.e. in the chamber CH, only a jet of particles JP remains. With an aerodynamic lens, on the other hand, one can typically have a vacuum in the chamber CH defined by a pressure between $10^{-3}$ mbar and 1 mbar. This allows to ensure an optimal operation.

Instead of the aerodynamic lens LA, a nozzle could be provided (not shown). With a nozzle, with the same objective of ensuring an optimal operation, one can typically have a vacuum in the chamber CH defined by a pressure between $10^{-3}$ mbar and 1 mbar.

The device D also comprises a laser L capable of emitting a laser beam FL in the form of pulses.

Associated with this laser L is an optical device DO arranged to focus the beam FL in the chamber CH, transversely to the direction DP of propagation of the particle jet JP. In the case shown in the figures, the laser beam FL is perpendicular to the direction DP of propagation of the particle jet JP.

This allows to create a plasma in a focal volume VF by the interaction between the laser beam FL and the particles $N_P$ in the jet JP of particles, plasma which emits other particles characteristics of the interaction between the laser beam FL and the particles in the jet. These other particles can be ions, electrons or photons.

The fact of operating in a vacuum in the chamber CH where the interaction between the laser beam FL and the particles $N_P$ of the jet JP takes place allows to individually detect biological particles of very small sizes, typically less than a few hundred nanometres and in particular of a size less than or equal to 200 nm, less than or equal to 150 nm and even less than or equal to 100 nm, without difficulty. It should be remembered that a virus is typically around 100 nm in size.

Figure 3:
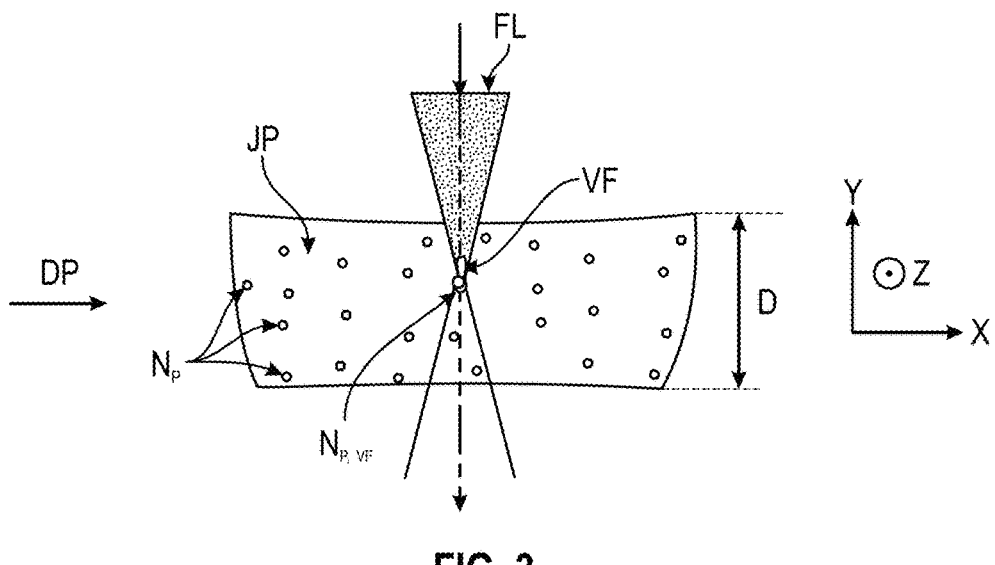
FIG. 3 shows schematically an area of interaction, within the device shown in FIG. 2, between a laser beam and a particle jet formed with the particles coming from a sampling of ambient gas comprising biological particles.

Reference can be made in particular to FIG. 3.

For the application to biological particles, densities of $10^3$ to $10^7$ particles per cm3 in the particle jet are typical. The particle density in the particle jet depends on the particle density in the ambient gas. It also depends on the nature and the size of the particles. For biological particles (e.g. viral particles) of the order of 100 nm in diameter, attached to receptors marked with metallic nanoparticles of 50 nm, for example, a well-collimated particle jet with a diameter D of the order of 100 μm is obtained, which allows to observe a density of biological particles of the order of $10^6$ to $10^7$ particles/cm3 in the jet.

The focal volume may typically be of the order of $10^4$ μm$^3$.

The Laser L can for example be a fibre laser.

Its repetition frequency (of the pulses) can generally be between 1 kHz and 1 Mhz. A minimum repetition frequency is of interest in order to characterise a number of aerosol particles sampled in a reasonable time. A much higher repetition rate of the order of one Mhz may be of interest when the concentration of particles in the gas sampled by the sampler is relatively low, in order to increase the probability of encountering a particle in the focal volume VF at each shot or laser pulse.

The minimum intensity to be implemented at the level of the focal volume is typically of the order of 10 GW/cm$^2$. This corresponds roughly to the intensity required to produce a plasma in the focal volume VF. To achieve this, the intrinsic characteristics of the laser L can obviously be used, but also, alternatively or in addition, the characteristics of the optical device DO.

The optical device DO may in particular be in the form of optical lenses or simply a microscope objective.

Typically, a fibred laser L operating at 1065 nm, with a pulse energy of about 0.2 mJ, associated with a 10× magnification microscope objective DO, allows to provide the minimum intensity of 10 GW/cm$^2$ in the focal volume VF.

Beyond the focal volume VF, i.e. after interaction with the particles of the particle jet JP, the laser beam FL is advantageously recollimated by an optical device DOR, referred to as recollimation, for example in the form of a set of lenses. The recollimated laser beam FL can then be sent to a means (not shown in the attached figures) capable of measuring the power of the laser beam FL. This allows to ensure, a posteriori, that the power theoretically injected by the laser L is indeed that provided by this laser L.

The device D also comprises at least one detection device DD comprising a means MC for collecting the particles emitted by the plasma and a means MAS for performing a spectrometric analysis of these particles.

The means MC for collecting the particles emitted by the plasma can be of various designs.

However, within the scope of the invention, it is advantageous to envisage, as a collection means, a plurality of N optical fibres $FO_1$, $FO_2$, $FO_3$, . . . , $FO_{N-1}$, $FO_N$, with N a natural number strictly greater than the unity, one end $E_1$, $E_2$, $E_3$, . . . , $E_{N-1}$, $E_N$ of each optical fibre $FO_1$, $FO_2$, $FO_3$, . . . , $FO_{N-1}$, $FO_N$ being arranged for this purpose around the focal volume VF, and pointing towards it.

Figure 4A:
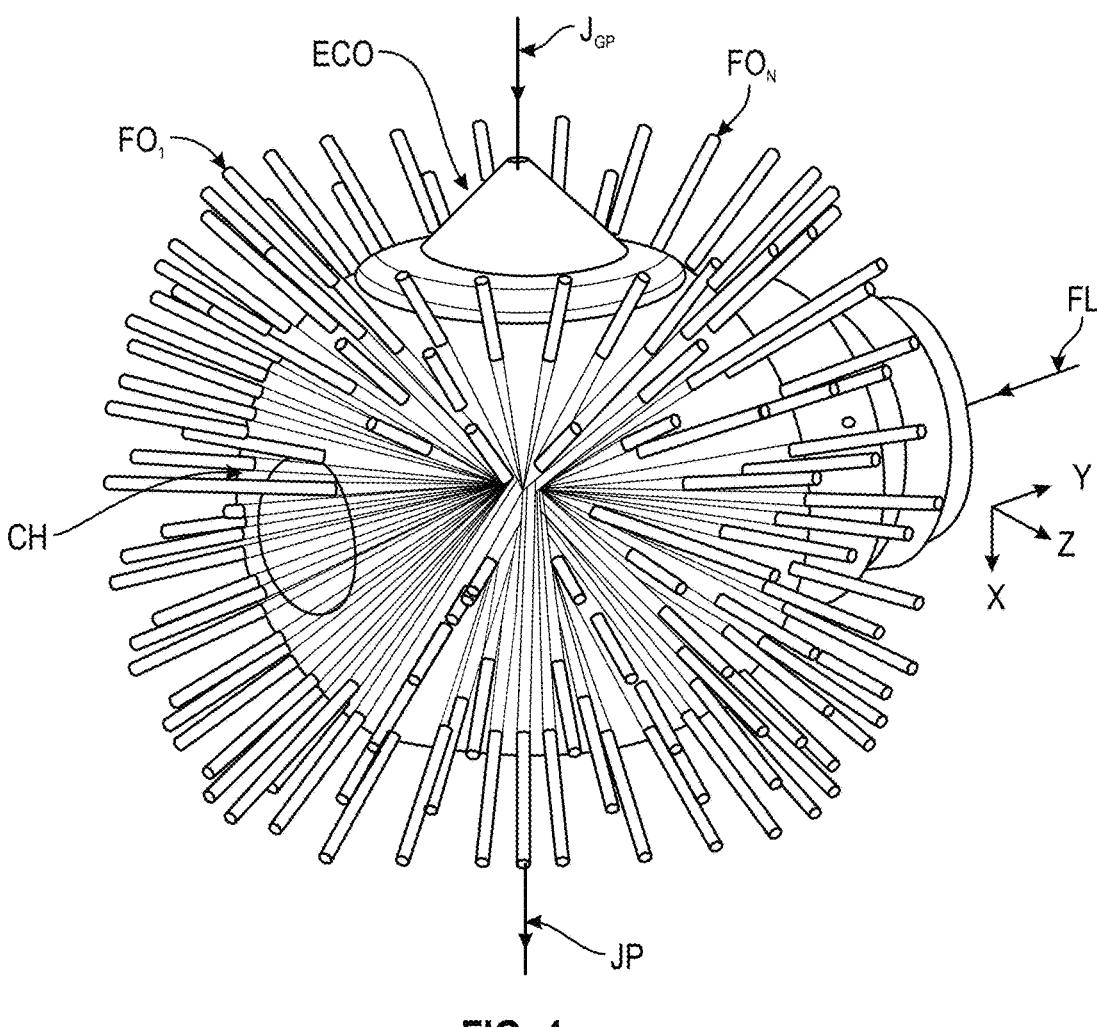
FIG. 4*a* is an external perspective view of a portion of the characterisation device shown in FIG. 2, portion in which there is shown a means for collecting, in the form of a plurality of optical fibres, particles generated by an interaction between a laser beam of said device with the particles of the aerosol.
Figure 4B:
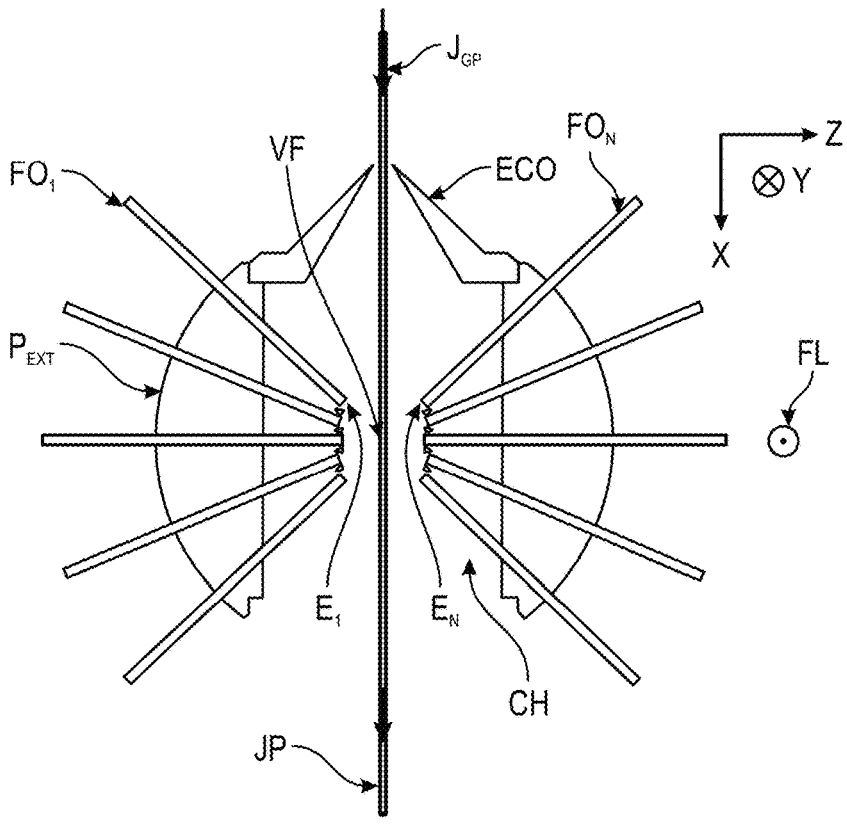
FIG. 4*b* is a view in a first cross-sectional plane of FIG. 4*a;*
Figure 4C:
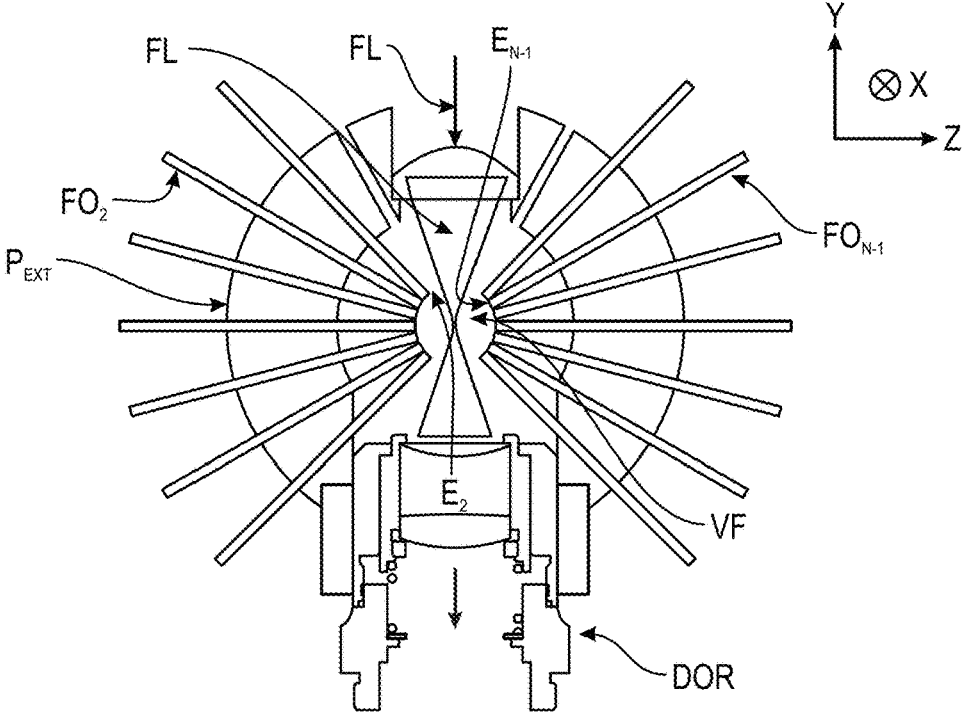
FIG. 4*c* is a view in a second cross-sectional plane of FIG. 4*a;*

This possibility is shown in different cross-sectional views of the device D in FIGS. 4(a) to 4(c).

The advantage of providing a multitude of optical fibres is that, in particular with reference to the use of a single optical fibre for the collection of the particles emitted by the plasma, the number of particles collected can be multiplied. This then allows to increase the sensitivity of the detection device DD. It is understandable that the greater the number of optical fibres, the greater the sensitivity.

Advantageously, a chamber CH may also be provided, the external wall P EXT of which is spherical in shape. In this case, the optical fibres FO, mounted on the wall of the chamber CH, can be arranged on this sphere to best cover the maximum solid angle of $4\pi$ steradians around the focal volume VF where the plasma is generated. This arrangement allows to increase the sensitivity of the detection device DD compared to any other arrangement for a given number N of collection optical fibres. The end of each optical fibre $FO_1$, $FO_2$, $FO_3$, . . . , $FO_{N-1}$, $FO_N$ may advantageously be located at a distance of a few millimetres from the centre of the focal volume VF, the most appropriate adjustment value depending in particular on the core diameter of the optical fibres used.

As a non-limiting example, here is an example of a possible implementation. N=158 optical fibres mounted on a spherical external wall $P_{EXT}$ of the chamber CH. Each optical fibre has a core diameter of 1 mm. Such an arrangement theoretically allows the collection of 44% of all the particles emitted by the plasma when the respective ends $E_1$, $E_2$, $E_3$, . . . , $E_{N-1}$, $E_N$ of the different optical fibres are arranged between 4 mm and 6 mm from the centre of the focal volume VF. With reference to a collection means comprising a single optical fibre, the core diameter of which is 600 microns and the collection end of which is located 4 mm from the centre of the focal volume VF, the quantity of particles emitted by the plasma that are collected is theoretically multiplied by 317.

It is of course possible, as an alternative, to use a single optical fibre for performing the collection, but in this case the detection loses sensitivity.

Different options are available for the spectrometric analysis means MAS, MAS'.

Figure 5A:
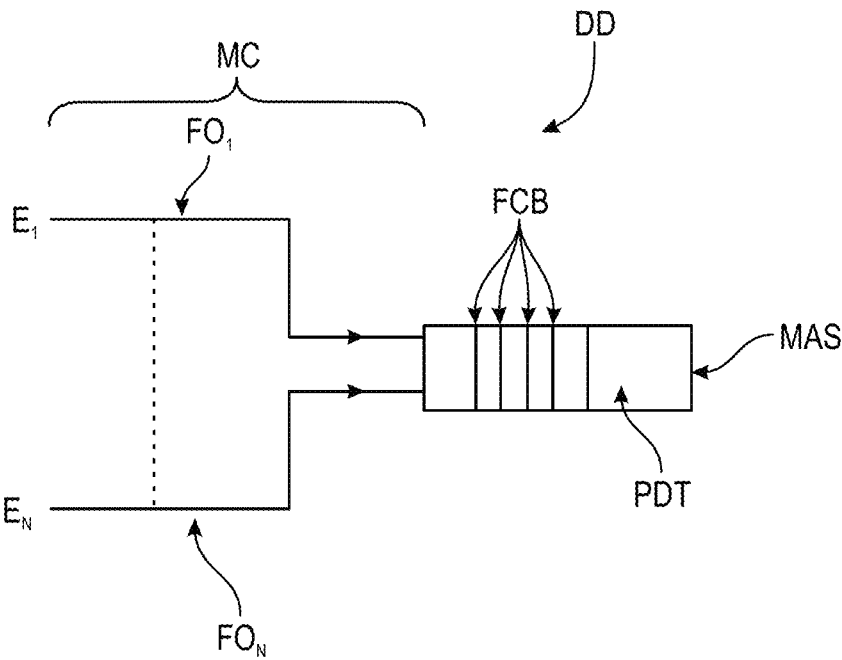
FIG. 5*a* is a schematic representation of a detection device, comprising the optical fibre collection means shown in FIGS. 4*a* to 4*c;*

Thus, according to a first option represented in FIG. 5(a), a spectroscopic analysis means MAS can be envisaged comprising at least one filter FCB of the notch type, capable of ensuring a filtering in a given wavelength band and at least one photodetector PDT, for example of the electron photomultiplier type. It can be used in particular the PMT H12775 proposed by the company Hamamatsu: https://www.hamamatsu.com/eu/en/product/type/H12775/index.html.

The notch filter thus selects a specific spectral domain and the intensity of the light (among the particles emitted by the plasma, there are photons) in this spectral domain is determined by the photodetector PDT.

For example, if we consider 4 spectral bands A, B, C and D, we will obtain the intensity of the signal in each of the bands considered, i.e. $I_I$ respectively, with I=A, B, C or D depending on the spectral band considered. For this purpose, it is necessary to provide a plurality of notch filters FCB ensuring a selection in distinct bands and as many photodetectors PDT, in particular of the electron photomultiplier type, as there are filters FCB.

One can also measure the overall intensity $I_G$ of the signal, i.e. the intensity taken for all the bands A, B, C and D and over a long accumulation time.

Alternatively, for each spectral band A, B, C and D considered, the number of events $N_{EI}$ can be counted, with I=A, B, C or D depending on the spectral band considered (independently of any intensity measurement).

These different data, $N_{EI}$, $I_I$, and $I_G$ are related to distinct physical quantities of the particles in the particle jet that are being analysed.

Thus, the number of $N_{EI}$ events can be related to the number of particles in the particle jet that are detected. In this way, the number of particles in the sampled ambient gas can be determined, i.e. a number concentration (i.e. volume) of particles in the sampled gas.

Furthermore, $I_I$ is proportional to the number of atoms of a given chemical element present in the individual particle analysed, i.e. the proportion of the corresponding chemical element in the individual particle analysed. It is therefore clear that the comparison of the intensities measured in the different spectral bands A, B, C and D allows to obtain respective proportions of the different chemical elements (4 if one has an intensity in the 4 spectral bands mentioned above) present in the individual particle analysed.

In addition, the overall intensity $I_G$ is proportional to the number of atoms present in the individual particle being analysed. In this way, a mass concentration of particles in the gas sampled by the sampler E can be determined.

It is therefore possible to obtain a certain amount of information on the biological particles present in aerosol form in the sampled gas.

From a practical point of view, this can be performed after calibration of the type of biological particle sought to be detected. This calibration must first be carried out in the laboratory so that the assembly of these data can be determined in the field.

Furthermore, it should be noted that the response time of a photodetector of the electron photomultiplier type is very low, typically of the order of a few nanoseconds. This type of detection is therefore particularly well suited to the use of a pulsed laser with a high repetition frequency, as in the case of the invention. No special precautions need to be taken to avoid the response/accumulation time of the photodetector PDT being longer than one cycle of the laser (cycle=time between two pulses of the laser).

Figure 5B:
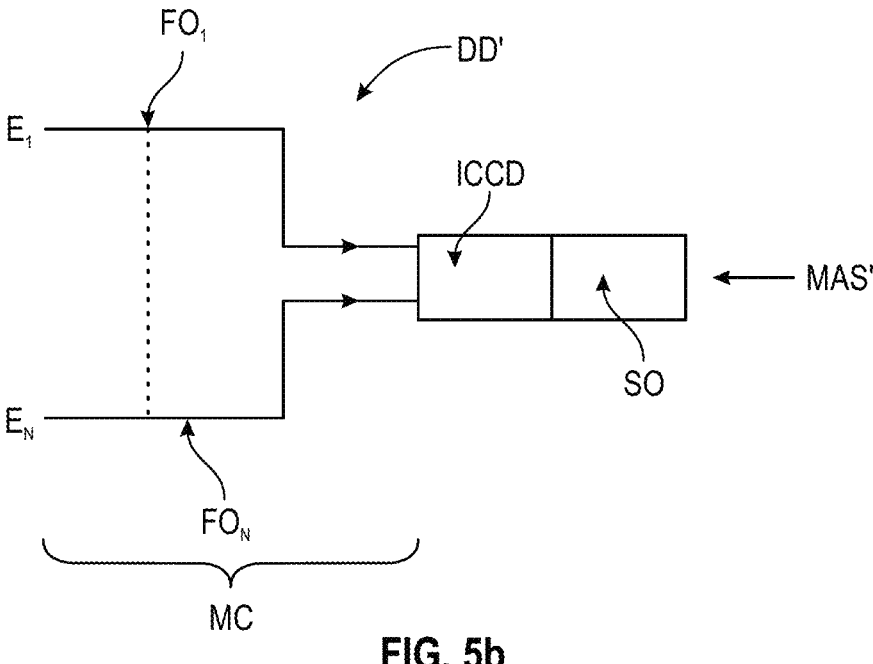
FIG. 5*b* is a schematic representation of an alternative detection device, also comprising the optical fibre collection means shown in FIGS. 4*a* to 4*c;*

According to a second option shown in FIG. 5(b), a spectroscopic analysis means MAS' can be envisaged comprising an optical spectrograph SO equipped with a camera of the intensified charge coupled device ICCD type.

This second option allows for a full spectral analysis over a very wide wavelength range.

It also allows a quantification of the chemical elements present in the individual particles of the particle jet that are analysed—after laboratory calibration.

This option finally allows to give access to the same information as those obtained with the first option, i.e. a mass concentration, a number concentration and a size of the aerosol particles.

In practice, the intensity $I_G$ can be obtained by selecting a mode referred to as "accumulation" on the camera ICCD.

On the other hand, to obtain $I_I$ and $N_{IE}$ (with I=A, B, C or D if we take the example presented above), a specific operating mode of the camera ICCD must be used to compensate for the slow acquisition speed of this camera. The response time of this type of camera is in the order of a hundred milliseconds, which is not necessarily compatible with the use of a pulse laser operating at a high repetition frequency. Also, the accumulation time of the camera ICCD must be maintained shorter than the time between two successive laser pulses, taking due account of the delay between a laser pulse and the start of acquisition by the camera ICCD, the gate width, i.e. the time during which the camera ICCD accumulates the signal, and the read-out time of the camera ICCD, i.e. the time during which the electronics associated with the camera read the information contained on the pixels of the camera ICCD.

In order to perform all these measurements, it must be ensured that the characterisation device D of the particles by laser-induced breakdown spectrometry only analyses an individual particle in the focal volume VF at a time. From a statistical point of view, it can be shown that the focal volume VF of the device D will only show an individual particle from the particle jet (see FIG. 3) if a particle is detected in at most 1 in 10 laser shots. In the case of the detection of biological particles, such as viruses or bacteria, this condition will in practice be de facto fulfilled, due to the concentration levels expected for such particles. Indeed, typically, the virus concentrations in the air can be very low, for example less than 100 viruses/cm³. However, such a concentration is often sufficient to infect a person.

Finally, it should be noted that it may be interesting to collect the particles for an ex situ analysis, confirming or completing, with different techniques, the results obtained in real time with the device D according to the invention.

Figure 6:
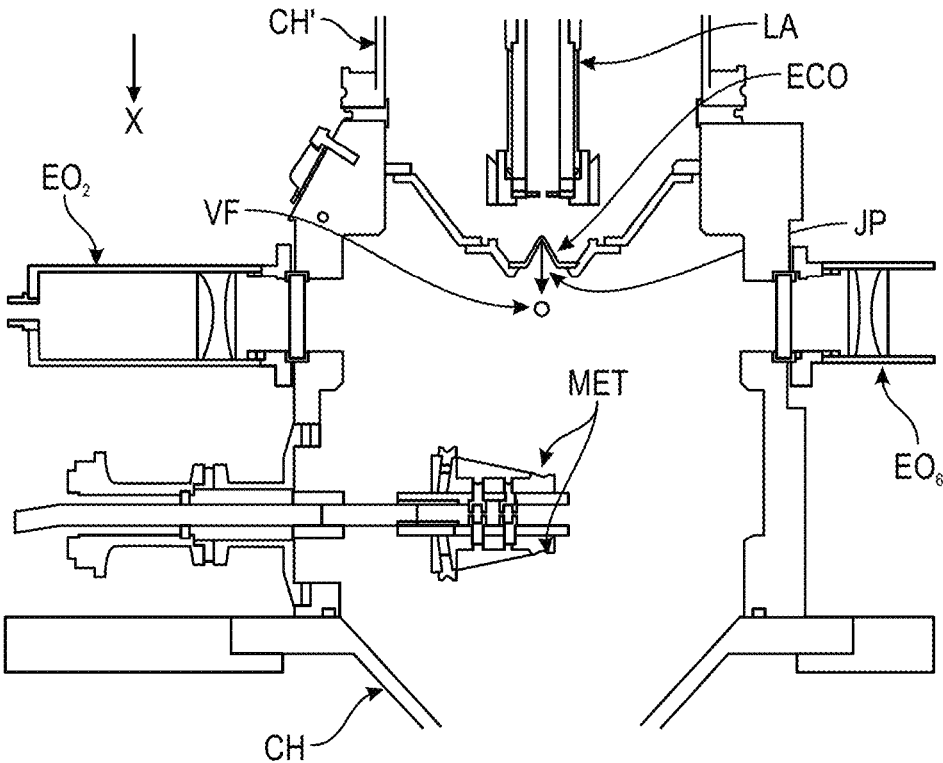
FIG. 6 is an enlarged cross-sectional view of a portion of the device shown in FIG. 2.

For this reason, and as can be seen in particular in FIG. 6, it is useful for the device D to provide a substrate holder MET, which may comprise a substrate (the deposit can then be used to make X-ray fluorescence, for example) and grids on either side of it (to carry out the transmission electron microscopy). The substrate holder is advantageously mounted so that it can rotate around its main axis, so that the grids can be exposed to the particle jet for relatively short periods of time. Indeed, for the purpose of performing transmission electron microscopy, it is then possible to study the actual agglomeration state of the particles in the jet (if layers of particles were deposited on these grids, as is performed on the substrate, this could not be considered).

As mentioned earlier, the measurement technique used allows to provide a certain amount of information about the biological particles sought to be detected.

However, the measurement technique described above does not necessarily allow the unambiguous detection of all types of biological particles. For example, by using different spectral bands A, B, C and D corresponding to carbon, hydrogen, nitrogen and oxygen respectively, and by measuring the intensity in each spectral band, it is possible that the respective proportions of each of these four types of chemical elements define biological particles that are actually quite distinct. Although it is possible in some cases to add a very specific spectral band to detect a very specific chemical element found exclusively in the biological particle of interest, this does not allow for the unambiguous identification of all biological particles.

It is therefore also the intention of the invention to provide such a possibility for any biological particle.

To this end, the method according to the invention provides, between the step a) and the step b), the following sub-steps:

aa) introducing the ambient gas into a chamber CHM referred to as mixing chamber, ab) introducing into the mixing chamber, in the form of an aerosol, at least one type of receptor for a specific molecule of the biological particles sought to be characterised, said at least one type of receptor being otherwise marked, ac) mixing, in the mixing chamber, the aerosol comprising said at least one type of receptor marked with a molecule specific to the biological particles sought to be characterised with the sampled ambient gas and comprising said biological particles to be characterised.

Figure 7:
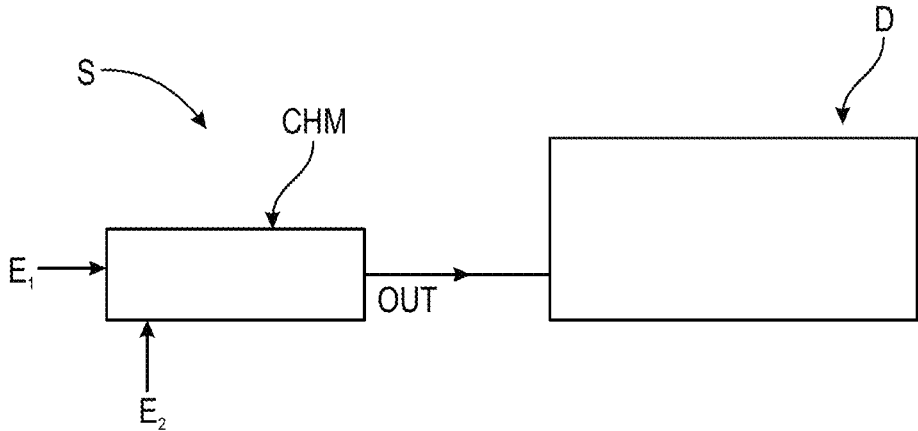
FIG. 7 is an overall schematic view of a biological particle characterisation system in accordance with the invention comprising, in particular, the device of FIG. 2.
Figure 8:
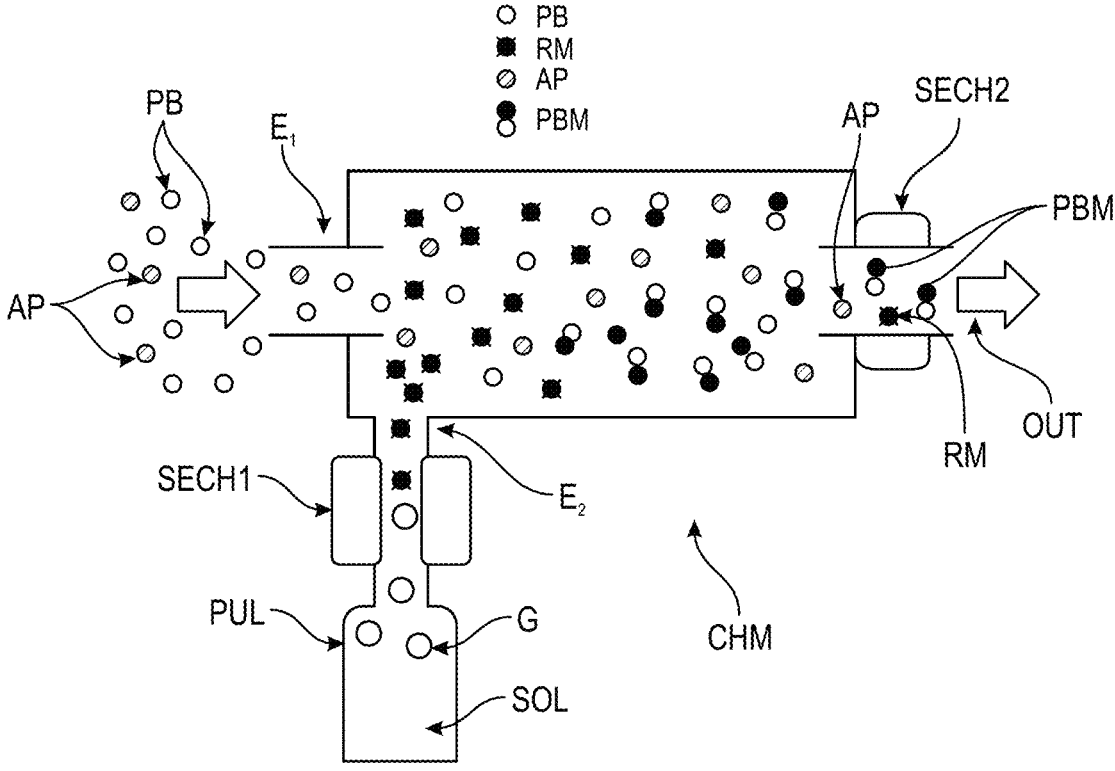
FIG. 8 shows a mixing chamber used with the device shown in FIG. 2 to form the system shown in FIG. 7.

A system S suitable for implementing the steps aa), ab) and ac) is shown in FIG. 7, in position relative to the device D for characterising said particles by laser-induced breakdown spectrometry shown in the preceding figures. In addition, a more detailed diagram of the mixing chamber CHM and the various elements allowing to feed it with various components is shown in FIG. 8.

The system S comprises means M for generating the aerosol of said at least one type of receptor marked with a molecule specific to the biological particles sought to be characterised.

The system S also comprises a mixing chamber CHM comprising:

a first inlet E1 for the gas to be sampled, a second inlet E2 for the aerosol generated by said means M to generate an aerosol of said at least one specific and marked receptor type of the biological particles sought to be characterised, and an outlet OUT for mixing said aerosol comprising said at least one type of receptor marked with a molecule specific to the biological particles sought to be characterised with the sampled ambient gas and comprising said biological particles to be characterised.

The interest of the mixing chamber CHM can be better understood from FIG. 8.

In this FIG. 8, on the left of the inlet E1, we see the surrounding gas comprising two types of particles, referred to as the biological particles PB sought to be characterised and all other particles AP. All these particles then enter the mixing chamber CHM through the inlet E1. Prior to the inlet E2 of the mixing chamber, a solution SOL of marked receptors is sprayed by a sprayer PUL in the form of droplets G (aerosol) containing the marked receptors. By passing through an (optional) dryer SECH1, the marked receptors RM are dried. The marked receptors RM then enter the mixing chamber through the inlet E2. Then, within the mixing chamber, the marked receptors bind to the specific molecules of the biological particle sought to be characterised to form a marked biological particle PBM. The objective of the mixing chamber is of course to obtain a maximum of marked biological particles. However, as can be seen in FIG. 8, at the level of the outlet OUT of the mixing chamber, there are marked receptors RM which have not been able to bind to biological particles PB as well as said other particles AP present in the surrounding gas sampled at the inlet E1 of the mixing chamber CHM.

The mixing chamber CHM may comprise at least one dryer SECH1, SECH2.

The dryer SECH1 can be arranged between the means M for generating the aerosol of said at least one type of receptor and the second inlet DE of the mixing chamber CHM. This allows the aerosol comprising said at least one type of marked receptor to be dried before the implementation of step ab). This drying step may be of interest when the specific molecule in question of the sought biological particle and/or its receptor can bind in a dry medium. Drying is necessary to use the device D located after the mixing chamber CHM.

Alternatively, the dryer SECH2 may be located at the level of the outlet OUT of the mixing chamber CHM—thus absent any dryer SECH1. This allows the formed mixture to be dried after the sub-step ac) before the step b) is implemented. This drying step can be envisaged when the specific molecule in question of the biological particle sought and/or its receptor can only bind in an aqueous medium. The drying is then only performed at the outlet of the mixing chamber, after the bonding has been performed.

Of course, if the dryer SECH1 is implemented, the dryer SECH2 can also be operated.

In a particular embodiment, the mixing chamber CHM may be a Goldberg rotary drum. Such a drum allows to increase the stability of the aerosols over time (the deposition of the aerosols on the walls is thus greatly prevented).

Advantageously, the marking of the receptor can be performed with a magnetic material (e.g. nanoparticles comprising Cobalt). In this case, after the sub-step ac), only those particles comprising this magnetic material can be selected by any suitable magnetic means, for example arranged at the outlet OUT of the mixing chamber CHM, before implementing the step b). In other words, only the particles comprising the magnetic material can then enter the device D of characterisation by laser-induced breakdown spectrometry, the others remaining in the mixing chamber CHM. Thus, following the scheme of FIG. 8, it can be ensured that said other particles AP sampled from the surrounding gas do not enter the device D for characterising said particles by laser-induced breakdown spectrometry.

Generating the marked receptor aerosol MR from a solution SOL, as shown in FIG. 8, is only one option.

However, when this option is used, the solution SOL can be water-based. However, where the nature of the receptor allows, the solution SOL may be alcohol-based, for example ethanol. This makes it easier to dry, as alcohol is more volatile than water. Eventually, this also allows any dryer SECH1 and/or SECH2 to be dispensed within the system S.

Advantageously, the step ab) may consist of introducing into the mixing chamber CHM, in the form of an aerosol, several distinct types of receptors for a molecule specific to different types of biological particles sought to be characterised, each type of receptor being marked. It is thus possible to have a first type of receptor capable of binding to a first type of biological molecule, for example SARS-CoV 1, and to have a second type of receptor capable of binding to a second type of biological molecule, for example SARS-CoV 2.

And to improve the characterisation, a different marking may be provided for each type of receptor. Thus, using our example, the marking for the receptor of a specific molecule SARS-CoV 1 could be silver nanoparticles and the marking for the receptor of a specific molecule SARS-CoV 2 could be gold nanoparticles.

The receptor/specific molecule pair can be diverse. In particular, it can be an antibody/antigen, avidin/biotin, lectin/polysaccharide or DNA-PNA (DeoxyriboNucleic Acid-Peptide Nucleic Acid) pair.

As previously mentioned, the marking will allow for any type of biological particle to be uniquely characterised, for example to uniquely characterise the SARS-CoV 2 bound to a receptor marked with gold nanoparticles.

At the level of the focal volume VF, a laser shot may indeed result in no particles being detected. In practice, this is the most frequent case, since it will concern at least 9 out of 10 laser shots.

It may also result in the detection, in some cases, of a particle AP present in the sampled gas, which is not biological. This is not relevant to the scope of the invention.

However, when a biological particle is present in the focal volume VF, it can be detected by performing a detection, for example, of the characteristic wavelengths of any of the following chemical elements: carbon (247.86 nm), hydrogen, nitrogen (between 746 and 776 nm) or oxygen (between 77.2 and 77.5 nm). These chemical elements are, however, present in all organic matter and this does not allow, in a good number of cases, and even by analysing the respective compositions of each of these chemical elements with a spectral band detection, to obtain a univocal information. This is why the detection of rarer chemical elements, such as phosphorus (identifiable at 178 nm, 214 nm or 254 nm) and present in SARS-CoV 2, can be added.

However, this does not allow for carrying out an unequivocal detection in all cases.

The presence of the marking therefore improves matters since, if well chosen (e.g. gold nanoparticles), it provides an easily identifiable signal LIBS in wavelength and otherwise intense (268 nm or 275 nm for the gold nanoparticles). However, as indicated with the description in FIG. 8, the marked receptors RM not bound to the biological particles PB sought to be detected (despite the presence of a mixing chamber), are likely to enter the device D operating by LIBS.

In order to ensure an unambiguous detection of the biological particle, it is therefore necessary to detect the characteristic signal of the marking and at the same time a characteristic signal of the biological particle in question. If we take the example of SARS-CoV 2, its presence can be assured without any doubt by detecting both a peak of intensity in the signal detected at a wavelength characteristic of the chemical element phosphorus and, at a wavelength characteristic of the gold nanoparticles, it being recalled that, by elaboration, the gold nanoparticles then mark a receptor (e.g.: antibody) of a specific molecule (e.g.: antigen) of SARS-CoV 2

Finally, it should be noted that, insofar as the invention allows the unambiguous detection of a biological particle, it also allows the number of detections of this biological particle per unit of time to be counted. A prior laboratory calibration (with which a count is made of the number of detections per unit of time of a given biological particle and for a known concentration of said biological particle) then allows, in use, to associate with this count a number concentration (number per unit of volume) of the biological particle in question (e.g.: virus) If we take the example of SARS-CoV2, we are thus able to determine the concentration and, consequently, the probability of an individual being infected.

The invention claimed is:

1. A method for characterising biological particles of a size less than or equal to 200 nm as an aerosol by laser-induced breakdown spectrometry, said method comprising the following steps:

a) sampling ambient gas, which comprises the biological particles sought to be characterised;

b) generating a jet of said particles (JAB) in a chamber (CH) under vacuum;

c) emitting a laser beam (FL) in the form of pulses with a repetition frequency comprised between 1 kHz and 1 MHz, and focusing said laser beam in said vacuum chamber (CH), transversely to a propagation direction of the particle jet (JP), to create, in a focal volume (VF), a plasma by the interaction between the laser beam (FL) and at most one individual particle ($N_P$) of the jet, said plasma emitting other particles, characteristics of the interaction between the laser beam and said individual particle of the jet;

d) collecting said particles emitted from the plasma; and e) performing a spectrometric analysis of these particles to finally characterise said biological particles.

2. The method according to claim 1, wherein between the step a) and the step b) the following sub-steps are implemented:

aa) introducing the ambient gas into a chamber (CHM) referred to as mixing chamber, ab) introducing into the mixing chamber, in the form of an aerosol, at least one type of receptor for a specific molecule of the biological particles sought to be characterised, said at least one type of receptor being otherwise marked, ac) mixing, in the mixing chamber, the aerosol comprising said at least one type of receptor marked with a molecule specific to the biological particles sought to be characterised with the sampled ambient gas and comprising said biological particles to be characterised.

3. The method according to claim 2, wherein, before the step ab), the aerosol comprising said at least one type of receptor marked with a molecule specific to the biological particles sought to be characterised is dried.

4. The method according to claim 2, wherein, after the sub-step ac), the formed mixture is dried before implementing the step b).

5. The method according to claim 2, wherein the marker being a magnetic material, after the sub-step ac), only the particles comprising this magnetic material are selected by any suitable magnetic means, before implementing the step b).

6. The method according to claim 2, wherein the aerosol comprising said at least one type of receptor marked with a molecule specific to the biological particles sought to be characterised is obtained from a sprayed solution (SOL) of said marked receptors.

7. The method according to claim 6, wherein the sprayed solution (SOL) is based on alcohol.

8. The method according to claim 2, wherein the step ab) consists of introducing into the mixing chamber (CHM), in the form of an aerosol, several distinct types of receptor for a specific molecule of the biological particles sought to be characterised, each type of receptor being otherwise marked.

9. The method according to claim 8, wherein each type of receptor is marked differently.

10. A system (D) for implementing a method according to claim 2, said system (S) comprising:

a means (M) for generating the aerosol of said at least one type of receptor marked with a molecule specific to the biological particles sought to be characterised;

a mixing chamber (CHM) comprising:

a first inlet (E1) for the gas to be sampled, a second inlet (E2) for the aerosol generated by said means (M) for generating an aerosol of said at least one type of receptor marked with a molecule specific to the biological particles sought to be characterised, and an outlet (OUT) for mixing said aerosol comprising said at least one type of receptor marked with a molecule specific to the biological particles sought to be characterised with the sampled ambient gas and comprising said biological particles to be characterised;

a device (D) for characterizing said particles by laser-induced breakdown spectrometry comprising:

a system (SG) for generating, from the gas coming from the mixing chamber (CHM), the jet of said particles (JP) in a chamber (CH) to which is associated a means for pumping (MP) the gas present in the chamber in order to create a vacuum in this chamber, a laser (L) capable of emitting the laser beam (FL) in the form of pulses with a repetition frequency comprised between 1 kHz and 1 MHz, with which is associated an optical device (DO) arranged to focus said laser beam in the chamber (CH), transversely to the direction of propagation of the particle jet (JP), and to create, in the focal volume (VF), said plasma by the interaction between the laser beam (FL) and the particles ($N_P$) of the jet, said plasma emitting other particles, characteristics of the interaction between the laser beam and said particles of the jet, at least one detection device (DD, DD') comprising a means (MC) for collecting the particles emitted by the plasma and a means (MAS, MAS') for performing a spectrometric analysis of these particles.

11. The system (S) according to claim 10, wherein the mixing chamber (CHM) comprises at least one dryer (SECH1, SECH2), arranged either between the means (M) for generating the aerosol of said at least one type of marked receptor and the second inlet (DE) of the mixing chamber (CHM), or at the level of the outlet (OUT) of the mixing chamber (CHM).

12. The system (S) of claim 10, wherein the mixing chamber is a Goldberg rotary drum.

13. The system (S) according to claim 10, wherein the means (MC) for collecting the particles emitted by the plasma comprises a plurality of N optical fibres ($FO_1$, $FO_2$, $FO_3$, . . . , $FO_{N-1}$, $FO_N$), with N a natural number strictly greater than the unity, one end (E1, E2, E3, . . . . EN) of each optical fibre ($FO_1$, $FO_2$, $FO_3$, . . . , $FO_{N-1}$, $FO_N$) being arranged around the focal volume (VF) and pointing towards this focal volume (VF) in order to ensure the collection of the particles emitted by the plasma.

14. The system (S) according to claim 13, wherein said optical fibres (FO) are mounted on an external wall ($P_{EXT}$), of spherical shape, of the chamber (CH).

15. The system (S) according to claim 10, wherein the means (MAS, MAS') for performing a spectrometric analysis of the particles emitted by the plasma comprises:

a plurality of notch type filters (FCB), capable of ensuring a filtering in a band of wavelengths distinct from each other, and a photodetector (PDT), for example of the electron photomultiplier type, associated with each notch filter.

\* \* \* \* \*